US010368743B2

(12) United States Patent
Gerrans et al.

(10) Patent No.: US 10,368,743 B2
(45) Date of Patent: *Aug. 6, 2019

(54) SYSTEM AND METHOD FOR VISUALIZATION OF OCULAR ANATOMY

(71) Applicant: Sanovas Intellectual Property, LLC, Reno, NV (US)

(72) Inventors: Lawrence J. Gerrans, San Anselmo, CA (US); Charles N. Wang, Santa Clara, CA (US)

(73) Assignee: Sanovas Intellectual Property, LLC, Reno, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 15/860,041

(22) Filed: Jan. 2, 2018

(65) Prior Publication Data

US 2018/0140190 A1    May 24, 2018

Related U.S. Application Data

(63) Continuation of application No. 14/481,254, filed on Sep. 9, 2014, now Pat. No. 9,854,971.

(51) Int. Cl.
*A61B 3/14* (2006.01)
*A61B 3/00* (2006.01)
*A61B 3/10* (2006.01)

(52) U.S. Cl.
CPC .............. *A61B 3/14* (2013.01); *A61B 3/0083* (2013.01)

(58) Field of Classification Search
CPC ................ A61B 3/00; A61B 3/10; A61B 3/02
USPC ......... 351/200, 205–206, 210, 221–223, 246
See application file for complete search history.

(56) References Cited

U.S. PATENT DOCUMENTS

| 5,847,804 A | 12/1998 | Sarver et al. |
| 8,226,601 B2 | 7/2012 | Gunday et al. |
| 8,540,667 B2 | 9/2013 | Gerrans et al. |
| 8,597,239 B2 | 12/2013 | Gerrans et al. |
| 2007/0159600 A1 | 7/2007 | Gil et al. |
| 2008/0136916 A1 | 6/2008 | Wolff |
| 2009/0103050 A1 | 4/2009 | Michaels et al. |
| 2009/0164007 A1 | 6/2009 | Van Heugten |
| 2011/0205491 A1 | 8/2011 | Koiwa et al. |
| 2012/0127427 A1 | 5/2012 | Guo et al. |
| 2012/0274900 A1 | 11/2012 | Horn et al. |
| 2013/0050070 A1 | 2/2013 | Lewis et al. |
| 2013/0155376 A1 | 6/2013 | Huang et al. |
| 2013/0215383 A1 | 8/2013 | Siminou |

FOREIGN PATENT DOCUMENTS

WO    2012088424 A1    6/2012

*Primary Examiner* — Dawayne Pinkney
(74) *Attorney, Agent, or Firm* — Forge IP, PLLC

(57) ABSTRACT

A system for visualization of eye anatomy includes at least one camera having a view vector along a first axis when in a first position, a housing to which the camera is coupled, wherein the housing engages the head of a patient such that the camera is positioned adjacent a patient's eye, and an actuator that moves the camera from the first position to a second position with a view vector along a second axis that is offset from the first axis. A method of visualization of eye anatomy includes engaging a patient's head with a housing, positioning at least one camera coupled to the housing adjacent an eye, wherein the camera has a view vector along a first axis when in a first position, and moving the camera to a second position with a view vector along a second axis offset from the first axis.

20 Claims, 18 Drawing Sheets

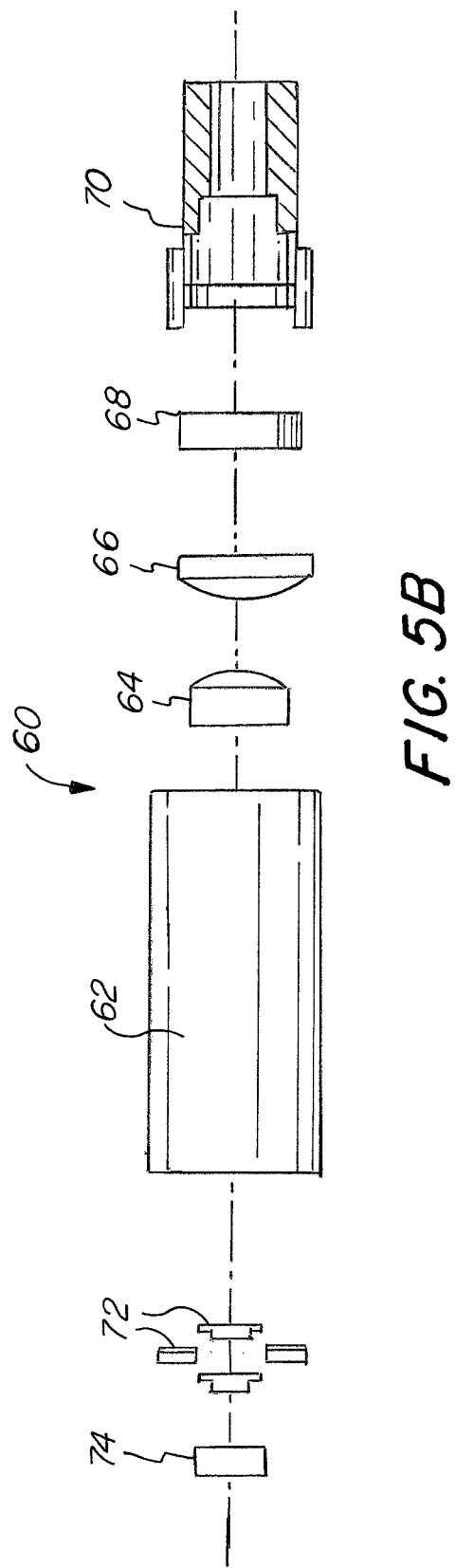

SYSTEM AND METHOD FOR VISUALIZATION OF OCULAR ANATOMY

FIELD OF THE INVENTION

The present invention relates to systems and methods for visualizing eye anatomy for diagnostic and therapeutic purposes. More specifically, the present invention relates to a system and method of visualizing eye anatomy by using one or more articulatable cameras to scan the eye using one or more spectrums and one or more wavelengths to provide wide angle fields of view of the eye anatomy to enable diagnostic and therapeutic interventions.

BACKGROUND OF THE INVENTION

Diabetic retinopathy is a disease characterized by damages to retina caused by complications of diabetes. The retina is a nerve layer that lines the back of the human eye. It is the part of the eye that captures the visual images and sends the images to the brain.

Diabetic retinopathy can be a serious condition and can often lead to poor vision or even blindness if not treated timely. Diabetic retinopathy is typically caused by changes in retinal blood vessels, which are induced by high blood sugar levels in a diabetic patient. These changes lead to improper formation of the blood-retinal barrier and make the retinal blood vessels become weak and more permeable.

A problem with diagnosing diabetic retinopathy is that it typically begins at the periphery of the retina, which is difficult to see, and then works its way towards the center of the retina, at which point it can be too late to treat and blindness can set in. Physicians often use microscope-like devices with or without an attached camera that have a fixed field of view (typically between 20-50 degrees) to try to diagnose diabetic retinopathy using the visible light spectrum. However, such examination sometimes does not reveal signs of retinopathy present at the periphery of the retina because of the limited field of view of these cameras. Additionally, they typically use cameras, e.g. CCD cameras that are very bulky and cumbersome to use. Thus, in order to see the periphery of the retina, it is desirable to increase the field of view when diagnosing retinopathy, while still utilizing a fairly simple device. It is also desirable to expand the number of spectrums and wavelengths to identify aspects of eye anatomy and pathology not found in the visible spectrum and associated wavelengths currently being employed.

There are few newer technologies that have been developed for more accurately diagnosing diabetic retinopathy. One such technology is a coherence tomography technology, as disclosed, for example, in US 2012/0127427 by Guo et al. This is an imaging technology similar to regular ultrasound. It utilizes an optical beam that is directed at eye tissue and a small portion of light that reflects from sub-surface structures is collected to re-create a 3D image of the retina. While this technique has many advantages, the equipment is very complex and expensive, making it not easily accessible to all patients and clinics. Further, a patient's pupil needs to be dilated during the procedure, which makes it more uncomfortable for the patient.

Another newer type of an imaging technique is a confocal scanning laser ophthalmoscope, which creates an image of the retina with a high degree of spatial sensitivity. Again, while this technique has many advantages, the required equipment is typically extremely cumbersome and expensive.

Yet another type of a retina imaging device is described in WO 2012/088424 by Busuioc et al. The device includes a camera having a body and at least one optical sensor provided on the body and configured to receive light directly from a lens of an eye. The optical sensor can be positioned closer or further away from the eye to focus the camera. While this device is rather simple and inexpensive, it still suffers from a number of disadvantages. For example, because the camera remains in the same position relative the surface of the eye, still only a limited angle of view of the eye anatomy can be captured. Additionally, because the camera does not utilize a lens, the quality of image of the eye anatomy obtained by the camera is fairly low.

Therefore, while various newer optical imaging techniques provide improved imaging capabilities, there is still a need for a simpler and more affordable device and method that allows for a simplified but accurate imaging of a person's retina to detect symptoms of diabetic retinopathy in addition to other eye diseases.

Additionally, it is possible that diseases of the body can be detected by finding trace elements of their existence by visualizing the anatomy of the eye. Alzheimer's disease is a neurodegenerative disease characterized by an increase of tiny inclusions in the nerve tissue, called plaques. These plaques are found between the dying cells in the brain from the build-up of a protein called beta-amyloid. Beta amyloid protein has been found to aggregate in the lens of the eye. Accordingly, the ability to detect and measure beta amyloid aggregates in the eye creates an opportunity to detect and diagnose the onset of Alzheimer's disease.

Conformational diseases, which include more than 40 disorders, are typically caused by the accumulation of unfolded or misfolded proteins. Improper protein folding or a so-called misfolding, together with accrual of unfolded proteins, leads to the formation of disordered (amorphous) or ordered (amyloid fibril) aggregates. Characteristic late or episodic onset of the conformational diseases is caused by the gradual accumulation of protein aggregates and the acceleration of their formation by stress. The best studied conformational diseases are neurodegenerative diseases and amyloidosis, which are accompanied by the deposition of specific aggregation-prone proteins or protein fragments and formation of insoluble fibrils. Amyloidogenic protein accumulation often occurs in the brain tissues. For example, Alzheimer's disease is associated with deposition of amyloid-beta and Tau, scrapie and bovine spongiform encephalopathy is associated with accumulation of prion protein, and Parkinson's disease is associated with deposition of alpha-synuclein. The accumulation of unfolded or misfolded proteins, which leads to pathology, also takes place in a variety of other organs and tissues, including different parts of the eye. Some of the best studied ocular conformational diseases include cataract in the lens and retinitis pigmentosa in the retina. However, deposition and accumulation of unfolded or misfolded proteins also occurs in other parts of the eye causing various disorders. Ocular manifestation of systemic amyloidosis can also cause deposition of amyloidogenic proteins in different ocular tissues.

Therefore, it is also an objective of this invention to create an imaging device that utilizes one or more scanning cameras with one or more spectrums combined with one or more wavelengths to visualize naturally unfolded and misfolded proteins in eye tissues, as well as other biological material, and to detect their structures and molecular mechanisms underlying their involvement in diseases.

SUMMARY OF THE INVENTION

The system and method of the present invention provides a number of advantages over the known optical imaging systems. On one hand, it is inexpensive and easy to use, thereby not requiring highly specialized training of physicians and making it more affordable to clinicians and patients. On the other hand, the device of the present invention allows an examining physician to obtain a much wider field of view as compared to conventional imaging techniques, thereby making the early diagnosis of diabetic retinopathy more likely. In addition, the system and method provides clinicians the ability to use one or more spectrums and one or more wavelengths to visualize the anatomy of the eye.

In order to overcome the deficiencies of the prior art and to achieve at least some of the objects and advantages listed, the invention comprises a system for visualization of eye anatomy, including at least one camera having a view vector along a first axis when in a first position, a housing to which the at least one camera is coupled, wherein the housing is configured to engage the head of a patient such that the at least one camera is positioned adjacent an eye of the patient, and an actuator that moves the at least one camera from the first position to a second position, wherein the at least one camera, when in the second position, has a view vector along a second axis that is offset from the first axis.

In certain advantageous embodiments, the second axis is angularly offset from the first axis. In other advantageous embodiments, the second axis is substantially parallel to the first axis.

In certain embodiments, the system further includes a processor that processes image data captured by the at least one camera.

In some embodiments, the at least one camera includes a plurality of cameras positioned adjacent the same eye of the patient. In certain of these embodiments, each of the plurality of cameras moves separately from the other cameras. In additional of these embodiments, the plurality of cameras moves together as a unit.

In certain embodiments, the system further includes a screen coupled to the housing between the at least one camera and the eye, wherein the screen displays an image in at least one of a 2-D format and 3-D format to the user. In some of these embodiments, the image is a static image. In additional of these embodiments, the image is a dynamic image.

In some cases, the system further includes at least one illumination device positioned adjacent to the at least one camera. In certain of these cases, the at least one illumination device includes a light source having at least one of a visible, ultraviolet, infrared and near infrared spectrum.

In certain advantageous embodiments, the housing is a standalone unit further including a positioning member for positioning the eye relative to the at least one camera. In other advantageous embodiments, the housing is configured as eyewear further including one or more mounting members for positioning the eyewear on the patient's head.

In some embodiments, the system further includes a storage device that stores image data captured by the at least one camera.

In certain embodiments, the system also has a display coupled to the processor for displaying image data captured by the at least one camera to a physician.

In some cases, the actuator moves the at least one camera from the first position to a third position, wherein the camera has a view vector along the first axis when in the third position.

In certain embodiments, the at least one camera includes at least one lens and at least one imaging sensor. In some of these embodiments, the imaging sensor is a CMOS sensor.

In some embodiments, the actuator includes a track coupled to the housing and a moving member coupled to the at least one camera, wherein the moving member moves along the track.

In certain embodiments, the actuator is a ball and socket type actuator that enables rotary movement of the at least one camera in all directions.

In some cases, the at least one camera captures a field of view of at least 180 degrees when moved from the first position to the second position.

In some embodiments, the eye is a first eye of the patient, further comprising at least one additional camera coupled to the housing such that, when the at least one camera is positioned adjacent the first eye of the patient, the at least one additional camera is positioned adjacent a second eye of the patient.

In some cases, the at least one camera adjacent the first eye moves separately from the at least one additional camera adjacent the second eye, and in other cases, the at least one camera adjacent the first eye and the at least one additional camera adjacent the second eye move together as a unit.

In certain embodiments, the system further includes a tracking system configured to track movement of the eye. In additional embodiments, the system further includes a tracking system configured to track movement of at least one structure and/or material within the eye.

A method of visualization of eye anatomy is also provided, including the steps of engaging a patient's head with a housing having at least one camera coupled thereto such that the at least one camera is positioned adjacent to an eye of the patient, wherein the at least one camera has a view vector along a first axis when in a first position, and moving the at least one camera to a second position, wherein the at least one camera, when in the second position, has a view vector along a second axis that is offset from the first axis.

A method of visualization of eye anatomy is also provided, including the steps of positioning at least one camera adjacent to an eye of a patient, wherein the at least one camera has a view vector along a first axis when in a first position, and moving the at least one camera to a second position, wherein the at least one camera, when in the second position, has a view vector along a second axis that is offset from the first axis.

In some embodiments, the method further includes the step of capturing image data by the at least one camera.

In certain advantageous embodiments, the second axis is angularly offset from the first axis. In other advantageous embodiments, the second axis is substantially parallel to the first axis.

In certain embodiments, the at least one camera includes a plurality of cameras. In some of these embodiments, the step of moving the at least one camera includes moving each of the plurality of cameras separately from the other cameras. In additional of these embodiments, the step of moving the at least one camera includes moving the plurality of cameras together as a unit.

In some cases, the eye is a first eye of the patient, and the method further comprises the step of positioning at least one additional camera adjacent a second eye of the patient.

In some embodiments, the at least one camera is coupled to a housing having a screen between the at least one camera and the eye of the patient, and the method further comprises the step of displaying an image via the screen. In certain of these embodiments, the image is a static image. In additional of these embodiments, the image is a dynamic image.

In certain embodiments, the method also includes the step of storing image data captured by the at least one camera on a storage device. In further embodiments, the method further includes the step of transmitting image data captured by the at least one camera to a remote location for display to a user and/or storage.

In some cases, the method further includes the step of displaying to a user image data captured by the at least one camera. In some of these embodiments, the image data displayed to the user is an image including two or more images captured by the at least one camera, wherein two or more images are at least partially combined to create the displayed image.

In certain embodiments, the method further includes the step of illuminating the eye anatomy via at least one illumination device positioned adjacent the at least one imaging device. In some of these embodiments, the at least one illumination device includes a light source having at least one of a visible, ultraviolet, infrared and near infrared spectrum.

In some embodiments, the method further includes the step of moving the at least one camera from the first position to a third position, wherein the camera has a view vector along the first axis when in the third position.

In some cases, the method further includes the step of measuring a diameter of an iris and adjusting the position of the at least one camera based on the measured diameter.

In certain embodiments, the method further includes the step of tracking movement of the eye and adjusting positioning of the at least one camera based on the movement of the eye. In other embodiments, the method further includes the step of tracking movement of at least one structure and/or material within the eye and adjusting positioning of the at least one camera based on the movement of the at least one structure and/or material within the eye.

Other objects of the invention and its particular features and advantages will become more apparent from consideration of the following drawings and accompanying detailed description.

BRIEF DESCRIPTION OF THE DRAWINGS

FIGS. 5A and 5B are exploded perspective views of a camera used in the system for visualization of eye anatomy of FIG. 1.

DETAILED DESCRIPTION OF THE INVENTION

Figure 1:
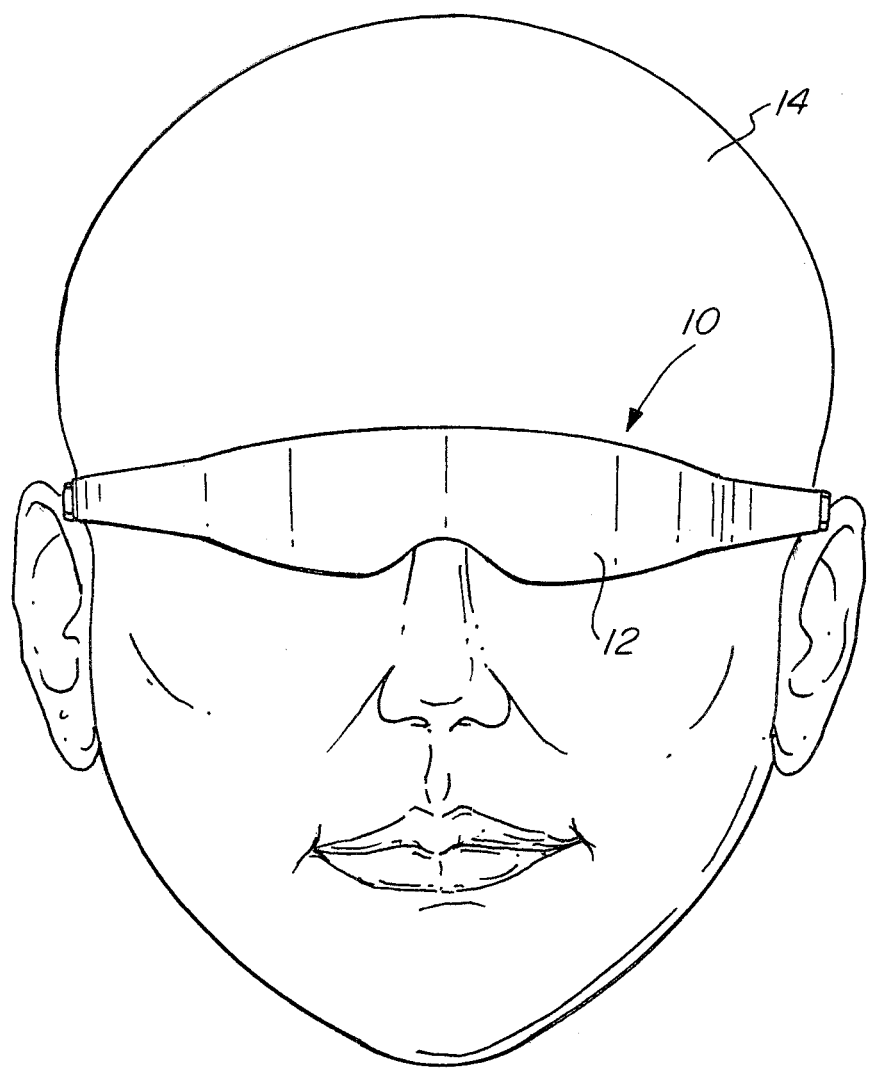
FIG. 1 is a front view of a system for visualization of eye anatomy in accordance with the present invention positioned on a person's head.
Figure 2:
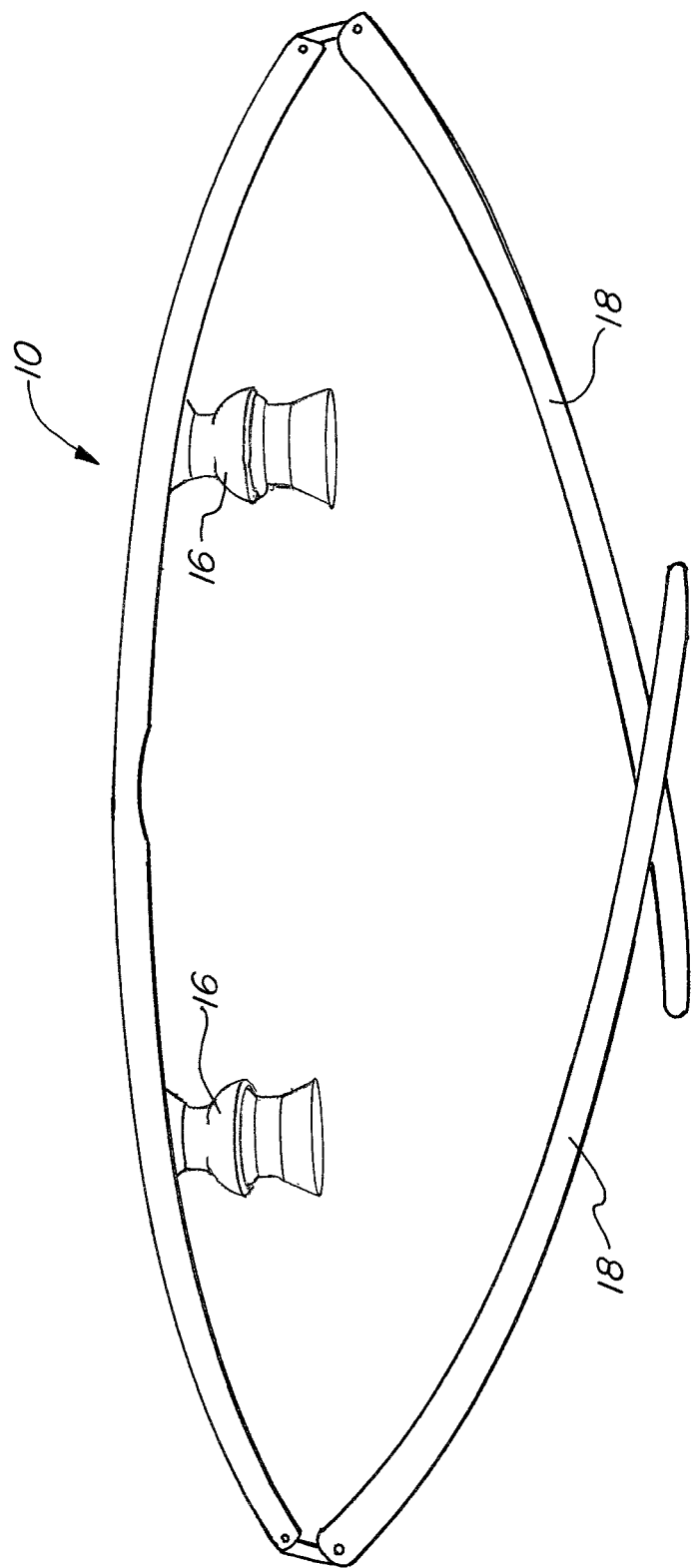
FIG. 2 is top view of the system for visualization of eye anatomy of FIG. 1.
Figure 3:
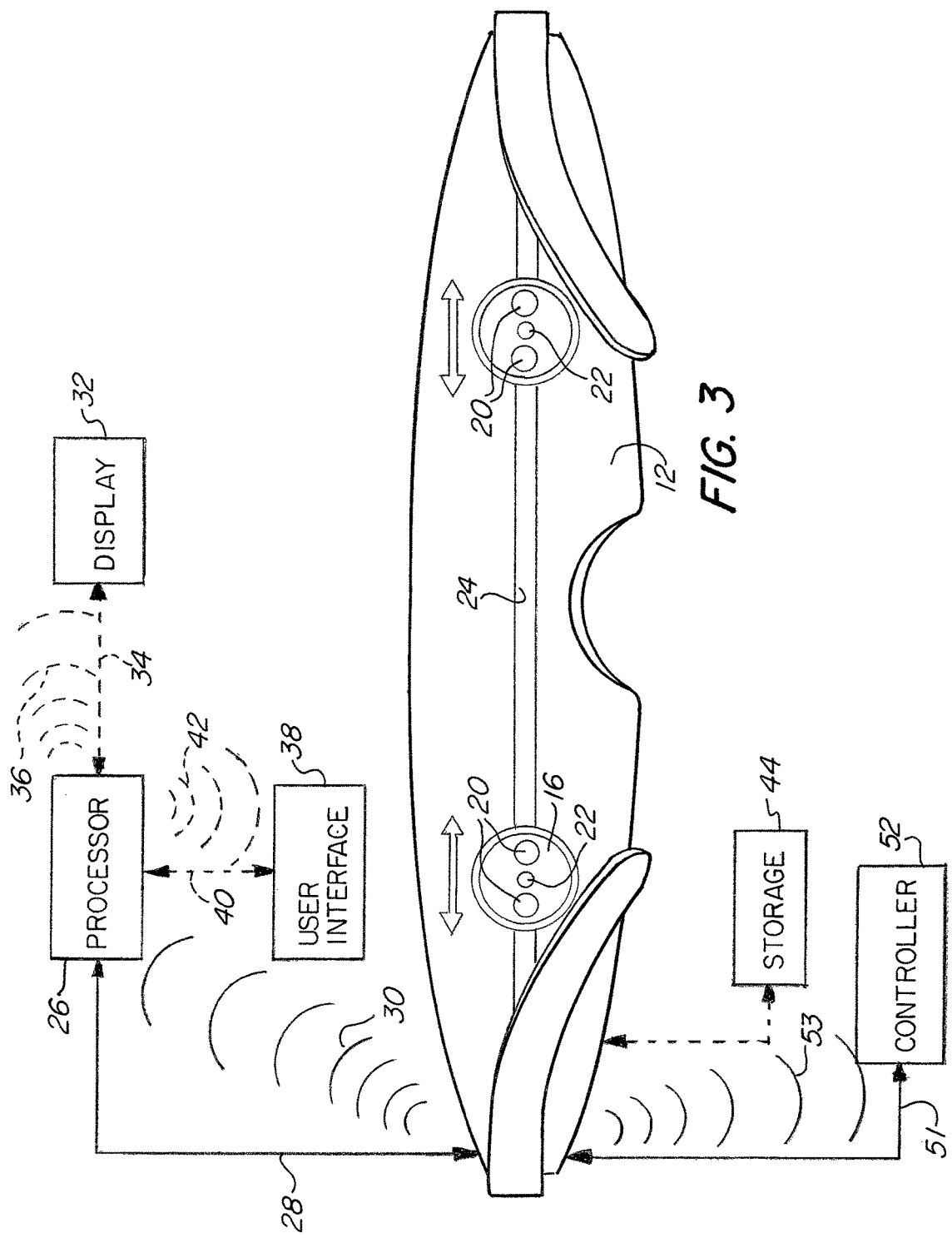
FIG. 3 is a rear view of the system for visualization of eye anatomy of FIG. 1.
Figure 4A:
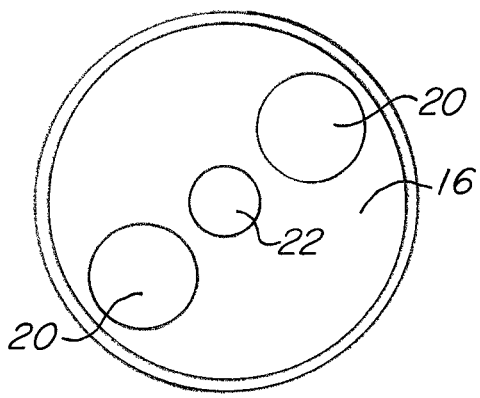
FIGS. 4A-4F are pupil views of various configurations of cameras and illumination devices of the system for visualization of eye anatomy of FIG. 1.
Figure 4B:
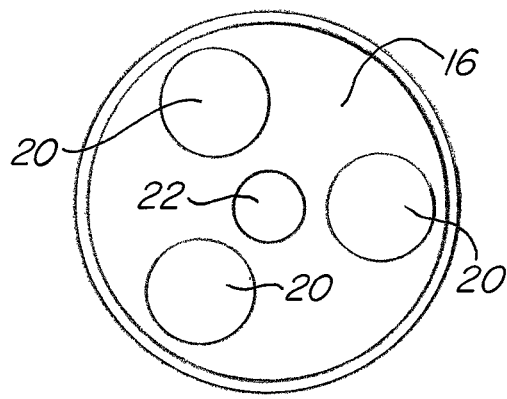
Figure 4C:
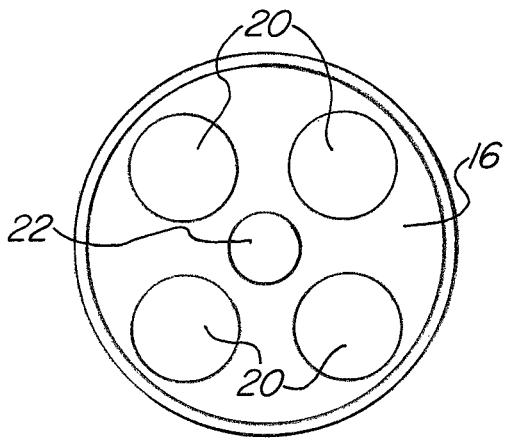
Figure 4D:
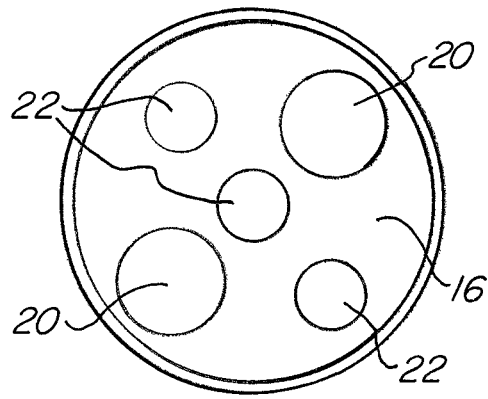
Figure 4E:
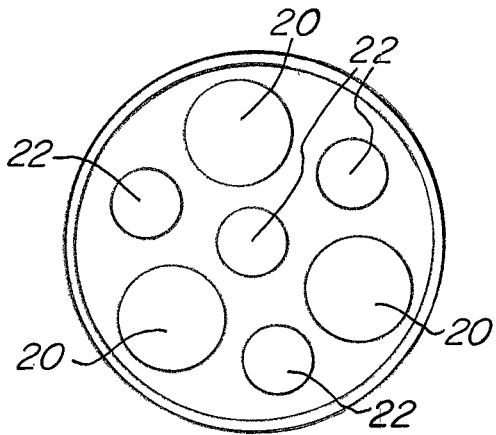
Figure 4F:
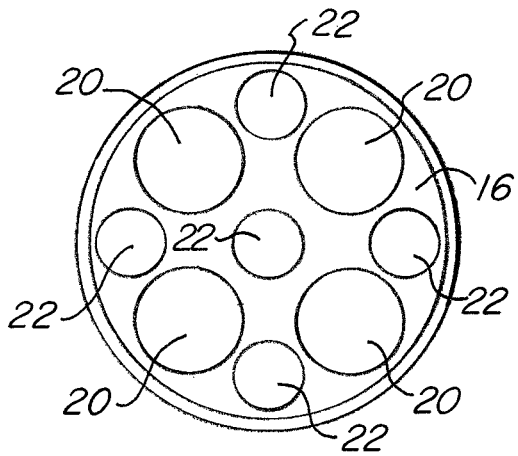

The basic components of one exemplary embodiment of a system for visualization of eye anatomy in accordance with the invention are illustrated in FIGS. 1-3. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system and method of the present invention uses an imager that is manually or mechanically articulatable by the physician to obtain a wide view angle of at least 180 degrees, thereby allowing examination of the periphery of the retina to detect early signs of diabetic retinopathy. It is understood that the system may also be used to image the eye anatomy for any other therapeutic and/or diagnostic purpose.

In some cases, it is useful to detect, observe and analyze various tissue deposits in the eye to diagnose and treat various diseases of the eye and other organs. For example, depositions of lipids, crystals, proteins and other artifacts in the eye may provide useful information regarding various diseases of the body. The ability to detect, measure and analyze these deposits by visualizing the anatomy of the eye creates an opportunity to detect and diagnose various diseases of the eye and other organs and systems.

The present invention can identify changes in the geography of the eye, including atrophy, emaciation, and swelling. Furthermore, the present invention allows for detection and analysis of various conditions of the eye, such as, for example, hydration, innervations, inflammation, circulation, nerve conduction, etc. Each of these conditions is typically caused by one or more diseases, and being able to visualize and measure these conditions in the eye provides very useful information regarding the cause, extent and diagnosis of various diseases of the body.

As shown in FIG. 1, the system for visualization of eye anatomy (10) is configured as eyewear that is placed on a person's head (14). The system includes a housing (12) that has two coupling members (16) for coupling one or more cameras to the housing, as shown in FIG. 2. The housing may be made with any suitable material, such as, for example, plastic or metal material, and may have any desirable shape. In one advantageous embodiment shown, the housing has a shape of typical eyeglasses. The housing further includes one or more mounting members (18), such as temples, for positioning the housing (12) on a person's head. It is noted that, in other embodiments, the housing may be configured as eye wear, or may be a hand-held device, as discussed in more detail below.

As illustrated in FIG. 3, each of the coupling members (16) is positioned on the housing (12) such that it is placed adjacent each eye of the person wearing the device (10). Each of the coupling members (16) includes at least one camera (20) coupled to the member (16). In some advantageous embodiments, such as shown in this figure, each of the coupling members (16) also includes at least one illumination device (22) positioned adjacent the cameras (20) to illuminate tissue inside the eye to facilitate better imaging of the eye anatomy.

Any desirable configurations of the cameras (20) and the illumination devices (22) may be provided in accordance with the present invention. Some exemplary configurations are shown in FIGS. 4A-4F. In the embodiments illustrated in these figures, two, three, or four cameras (20) may be used to image a single eye. The cameras (20) may be positioned in any desirable configuration, such as in line or in a shape of a triangle or a square. One, two, three, four or five illumination devices (22) may be used together with any number and configuration of the cameras (20), and the illumination devices (22) may be have any desirable orientation with respect to the cameras. It is noted that the numbers and configurations of the cameras and illumination devices shown in these figures are only exemplary, and that any other number and/or arrangement of the cameras and illumination devices may be used in accordance with the present invention.

The camera (20) may comprise any imaging device suitable for viewing the target area, such as a coherent fiber bundle or appropriate optical element and lens assembly in conjunction with an imaging sensor (e.g., CMOS, CCD), having a sufficiently small outer diameter, preferably about 0.75 mm-2.5 mm, and more preferably about 1 mm or less. For example, the system of the present invention may utilize a proprietary camera, such as is described in U.S. Pat. No. 8,226,601 to Gunday et al. and U.S. Pat. Nos. 8,597,239 and 8,540,667 to Gerrans et al. It is noted that, in some embodiments, only one camera may be used to image the anatomy of patient's one eye.

Figure 5A:
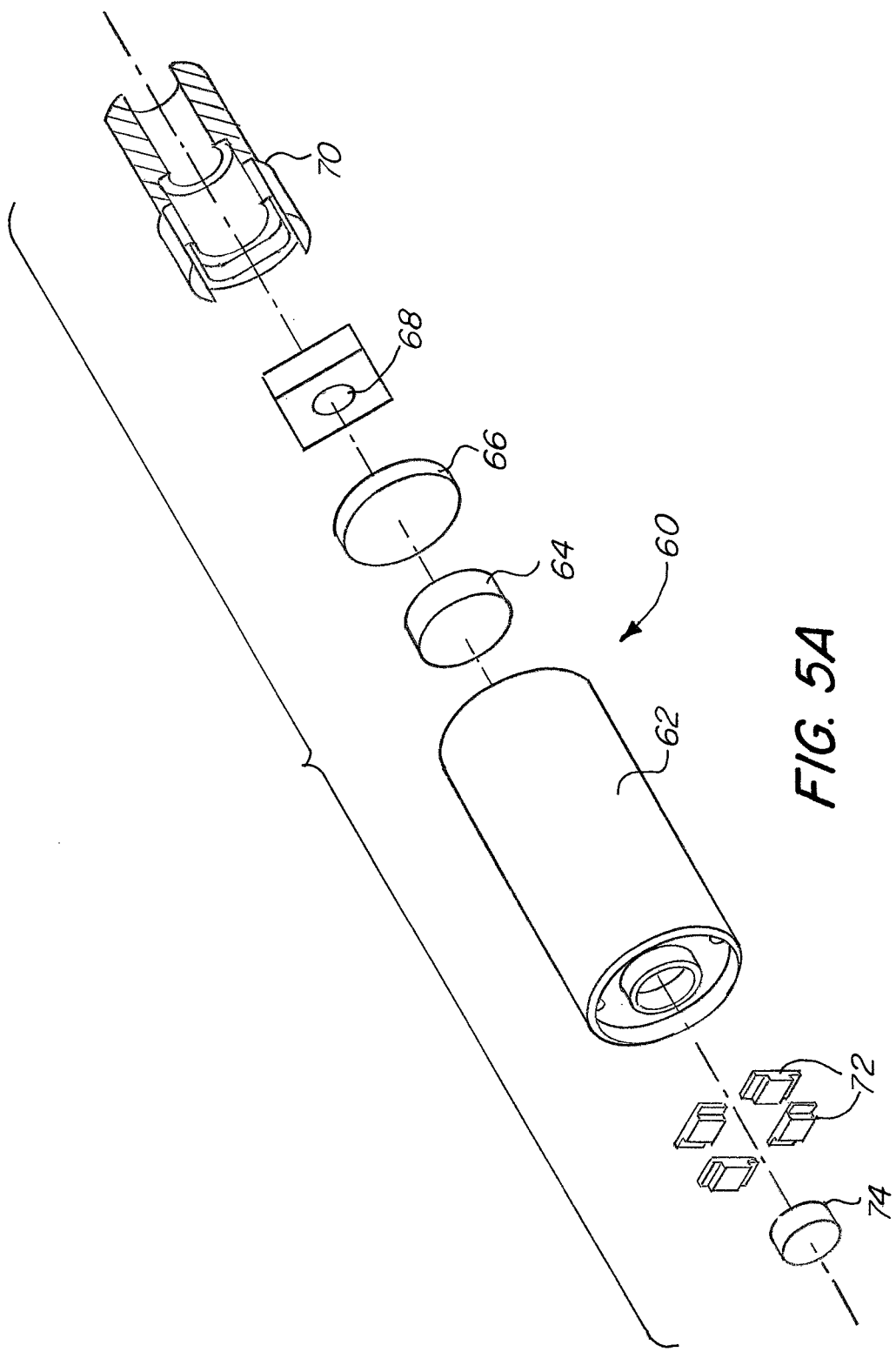

One advantageous camera embodiment is illustrated in FIGS. 5A and 5B. The camera includes a camera housing (62) that houses all camera components. The housing (62) is made with any suitable material, such as plastic or metal, and has any desired shape and size. The camera also includes one or more lens positioned in the housing. In the embodiment shown in these figures, the camera includes two plano-convex lenses (64) and (66) positioned opposite of each other such that the convex sides of the lenses are facing each other. It is understood that any other lens type and arrangement may be used in accordance with the present invention, as desired.

The camera (60) further includes an imaging sensor (68) positioned proximally from the lens (64) and (66). Any type of imaging sensor may be used. The imaging sensor (68) is coupled a sensor mount (70) to fixate the sensor inside the housing. In one advantageous embodiment, a CMOS sensor is used. The housing (62) also has one or more illumination devices (72), e.g. LEDs, lasers, and/or fiber optic cables, positioned distally from the lens. It is understood than other types of illumination devices may be used. The illumination devices emit various types of light, depending on desired application. For example, the illumination devices may emit ambient light, visible spectrum light, ultraviolet light, infrared light, near infrared light, etc. A distal end of the housing (62) has a pupil relay system (74) that seals the distal end of the housing to protect the camera components positioned in the housing.

It is understood that the camera design illustrated in FIGS. 5A and 5B is only exemplary and that any other camera design may be used with the system of the present invention. The camera is coupled to an actuator that enables a linear or rotational movement of the camera, as described in more detail below, to provide a larger angle of view.

As described above, the system of the present invention allows examination of the eye anatomy using light of various spectrums and various wavelengths. This allows for detection, visualization and characterization of various tissues, structures, and molecular compounds that may be present in the eye, which in turn lead to diagnosis of various eye and body diseases. This is due to the fact that various tissues and structures that may be present in the eye absorb and/or deflect light of various spectrum and/or wavelengths in different ways. Analysis of the light scattering thereby provides information about particular tissues and structures present in the eye. The system of the present invention also allows for detection and characterization of changes in eye anatomy over time, which may be caused by various diseases. The system is capable of measuring color saturation of the light emitted onto the target tissues and also measures scattering of light deflected from the target tissues in the eye.

As noted above, the system of the present invention may utilize a plurality of illumination devices or light sources. In some embodiments, all of the light sources emit light of the same spectrum/wavelength. In additional embodiments, each of the plurality of light sources emits light of a different spectrum/wavelength than the light emitted by other light sources. This allows for detection and characterization of various structures and conditions inside the eye, as described above.

In some advantageous embodiments, the system of the present invention utilizes a continuous wave/stream of light. In other advantageous embodiments, the system uses a pulsed light, wherein the light emitting devices positioned on the system adjacent the cameras emit pulses of light at a desired frequency. The cameras may capture image data after each pulse of light, or at particular intervals after a certain number of light pulses. In further advantageous embodiments, the same light sources may emit light in both continuous wave and pulsed waves, as desired, and/or some of the light sources may emit light continuously and other light sources may emit light in pulsed waves.

Referring back to FIG. 3, the system (10) further includes a processor (26) coupled to one or more cameras (20) for receiving and processing image data captured by the cameras. Any suitable processor may be used in accordance with the present invention. For example, the processor (26) may be a personal computer. The digital image data captured by the imaging sensor positioned on the cameras (20) is transmitted to the processor for analysis and for creating images that are displayed to the physician. One of the techniques that are may be utilized to process the captured digital data is spectroscopy, which analyzes interaction between matter and radiated energy. By utilizing spectroscopy techniques, it is possible to digitally process spectrums and wavelengths reflected from the eye to detect and characterize various elements present in the eye.

In one advantageous embodiment, the processor (26) is connected to the cameras (20) via a cable or wired connection (28). In additional advantageous embodiments, the processor (26) is connected to the cameras (20) via a wireless, e.g. cellular or satellite, connection (30), which is desirable if a physician is located remotely from a patient, whose eye anatomy is being examined. For example, the system of the present invention may be used by a patient in his or her home to capture images of the eye anatomy and then wirelessly transmit the data to the remotely located physician for analysis. Or the system of the present invention may be used by physicians located in field conditions, such as on a battle field, wherein there is no time or accessibility to analyze the captured eye anatomy data. The physicians utilize the cameras to capture the image data and then send it wirelessly to remote locations for analysis. In further advantageous embodiments, the captured image data may be stored in cloud storage, meaning that the digital data is stored in logical pools, with the physical storage typically spanning across multiple servers managed by a hosting company. This way, the data may be easily access from any location connected to the cloud storage, such as physicians' and patients' personal computers, tablets and smart phones.

Furthermore, the cameras (20) and/or the processor (26) may be connected to an external storage device, a removable storage device, and/or to an internet port. The image data captured by the cameras is stored on the storage device (44) and may be later retrieved by a user. In other advantageous embodiments, the processor (26) may have an internal storage device. Any suitable storage device may be used in accordance with the present invention.

In some embodiments, the image data is compressed before it is transmitted to the processor for processing or stored. In other words, the imaging data is encoded using fewer bits than the originally captured data to reduce resource usage, such as data storage space or transmission capacity. Once the compressed data is received by the processor, it is decompressed before it is displayed to the user to maintain the original quality of the captured images.

The system (10) may further include a display (32) coupled to the processor (26) via a cable connection (34) or via a wireless connection (36). The display (32) receives imaging data processed by the processor (26) and displays the image of the person's eye anatomy in 2-D format and 3-D format to a physician. Any suitable type of a display may be used in accordance with the present invention.

In one advantageous embodiment, such as shown in FIG. 3, the system (10) further includes a user interface (38) coupled to the processor (26). The user interface (38) may be a graphical user interface (GUI), a keyboard, or any other suitable device that allows a user to input information and commands. The user interface is connected to the processor via a cable connection (40) or via a wireless connection (42). In some embodiments, the user interface (38) is displayed on the display (32) as on overlay image.

The system (10) of the present invention further includes an actuator coupled to each camera for moving the camera in different directions. In particular, the camera can be moved from a first position, in which the camera has a view vector along a first axis, to a second position, in which the camera has a view vector along a second axis that is offset from the first axis, as further discussed below in reference to FIGS. 6B, 6D, and 6E. Movement of the camera from the first position to the second position allows the physician to obtain an increased field of view of the patient's eye, and in particular, the patient's retina. In advantageous embodiments, this increased field of view is at least 180 degrees. In some cases, the total, combined field of view is 200 degrees or more.

Figure 6A:
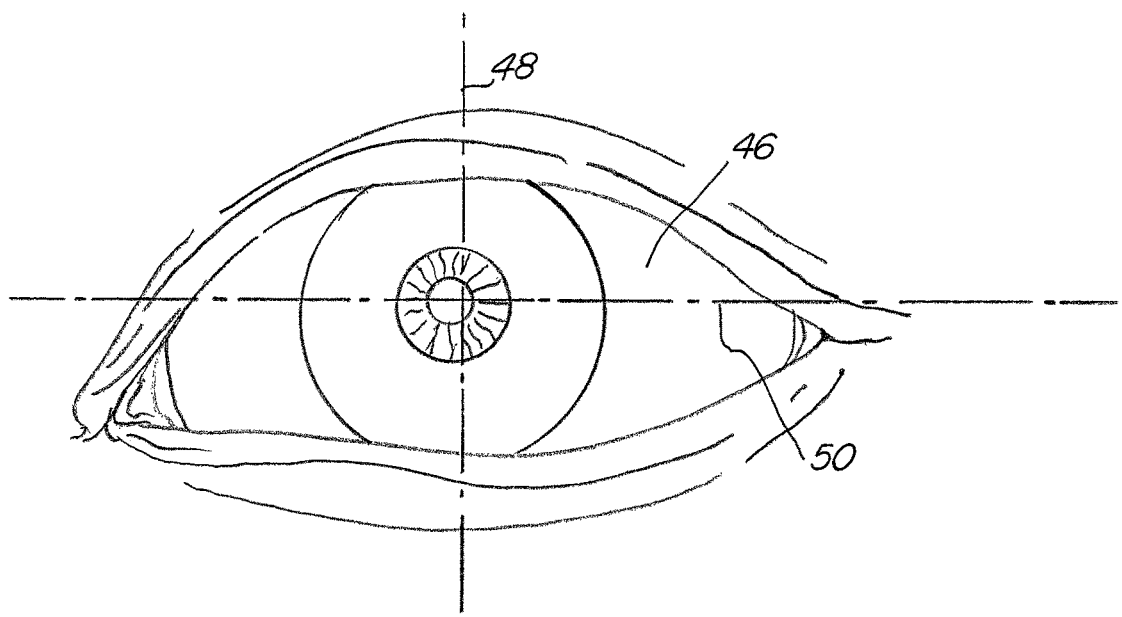
FIG. 6A is a schematic front view of a person's eye.

In one advantageous embodiment, the actuator is capable of moving the cameras in a direction substantially parallel to at least one of a horizontal axis (50) of the eye (46) and a vertical axis (48) of the eye (46), as shown in FIG. 6A.

Figure 6B:
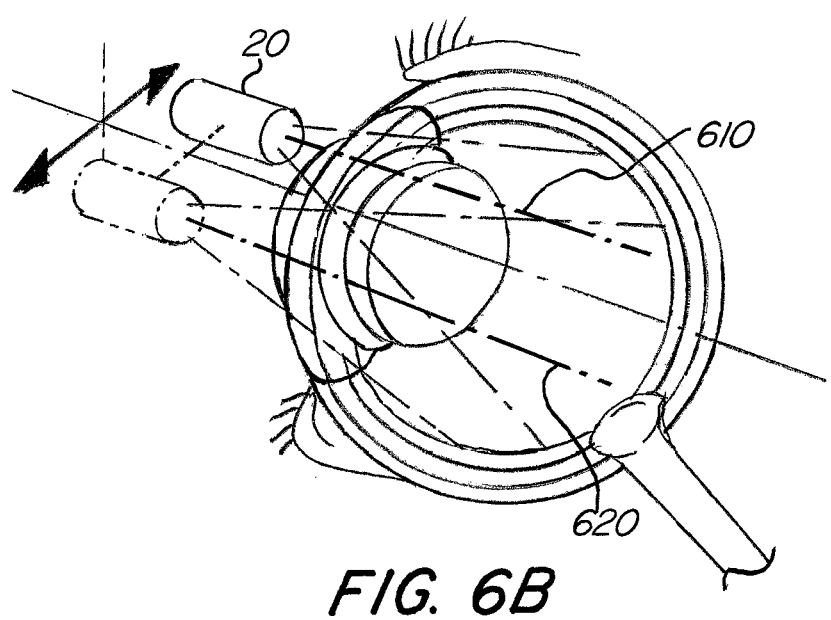
FIGS. 6B-E are partially isometric and schematic views of the camera of FIGS. 5A-B moving relative to the eye.

As shown in FIG. 6B, the camera (20) moves from a first position having a view vector along the first axis (610) to a second position having a view vector along a second axis (620), wherein the second axis (620) is substantially parallel to the first axis (610). This motion can be side to side, as depicted in FIG. 6B, the motion can also be up and down, as depicted in FIG. 6D, such that the camera (20) similarly moves from a first position having a view vector along first axis (640) to a second position having a view vector along second axis (650), wherein second axis (650) is substantially parallel to first axis (640). These motions can occur whether the camera (20) itself is pointed straight ahead or pivoted at an angle.

Figure 6C:
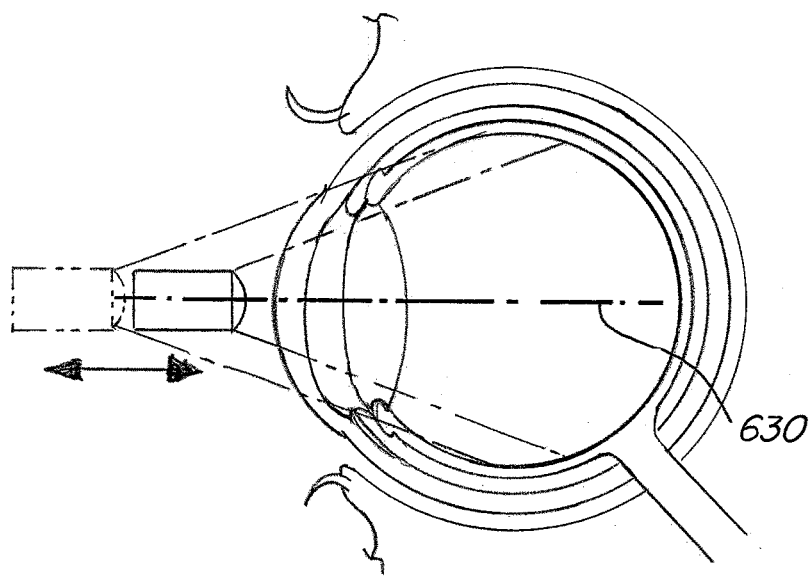
Figure 6D:
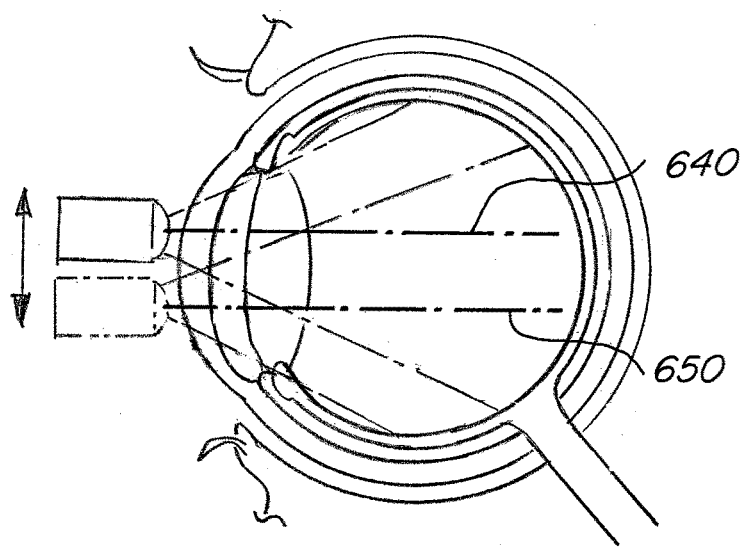
Figure 6E:
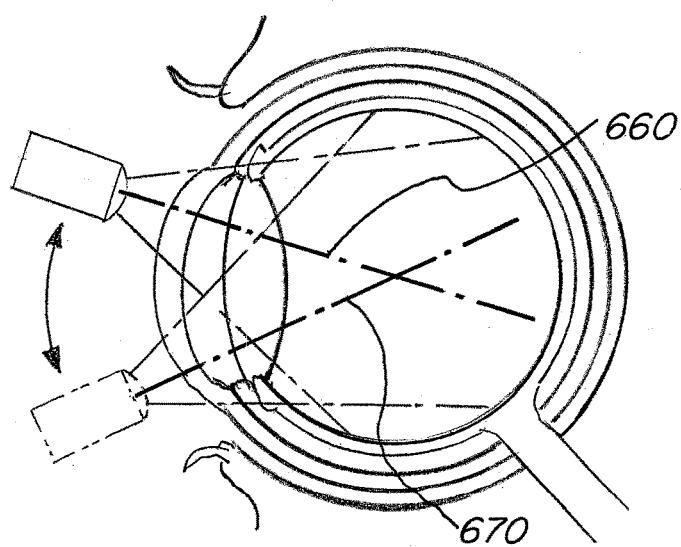

As shown in FIG. 6E, the camera (20) is moved from a first position having a view vector along a first axis (660) to a second position having a view vector along a second axis (670), wherein the second axis (670) is angularly offset from the first axis (660).

As shown in FIG. 6C, in additional advantageous embodiments, as discussed further below, the actuator is also capable of positioning the cameras at a desired distance from the eye. In these embodiments, the cameras move from the first position to a third position, in which the cameras have a view vector along the same axis (630) as when the camera is in the first position.

Figure 6F:
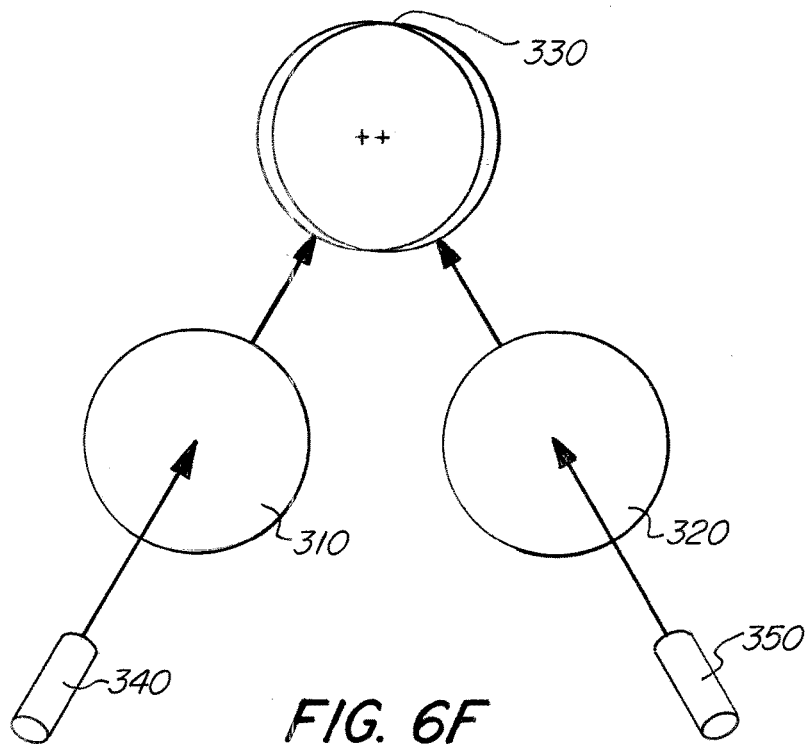
FIGS. 6F-H are schematic views of different types of images captured by the camera used in the system of FIG. 1.

In some advantageous embodiments, one or more mosaic cameras are used to capture an image of the eye anatomy. The mosaic cameras have the structure described above or any other suitable structure. Each camera (340, 350) captures an image (310, 320) of the eye anatomy. The captured images are then sent to the processor, which processes the image data and displays the image to the user on a display. The images (310, 320) from each camera are laid over one another to produce a single image (330), as shown in FIG. 6F, which is displayed to the user. This allows the user to see an image of the eye anatomy having different depths and/or 3D characteristics.

Figure 6G:
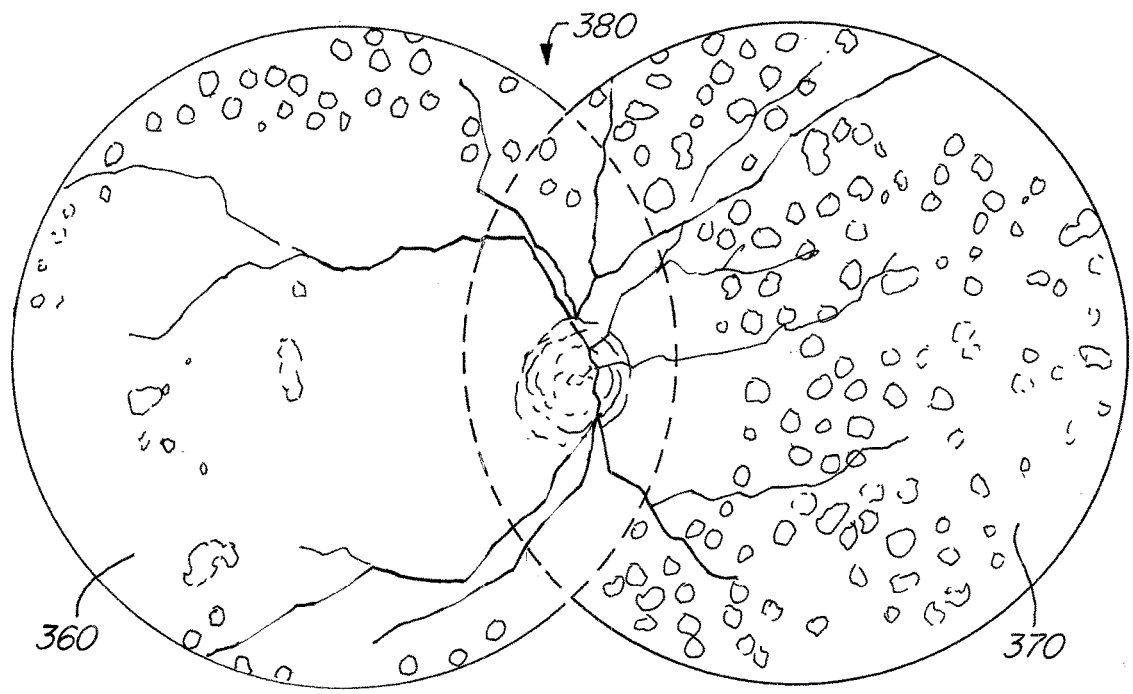

In additional embodiments, images captured by two or more cameras are "stitched" together when displayed to the user to provide for a more detailed image of the eye anatomy. For example, as shown in FIG. 6G, a first image (360) captured by a first camera and a second image (370) captured by a second camera are "stitched" or merged together to provide a single image (380), which is then displayed to the physician. This image (380) provides a much wider and detailed field of view of the eye anatomy as compared to a single camera image. It is understood that the images (360, 370) may be captured by the same camera positioned at different angles and/or distances from the eye, and then the images are combined to produce a stitched image.

Figure 6H:
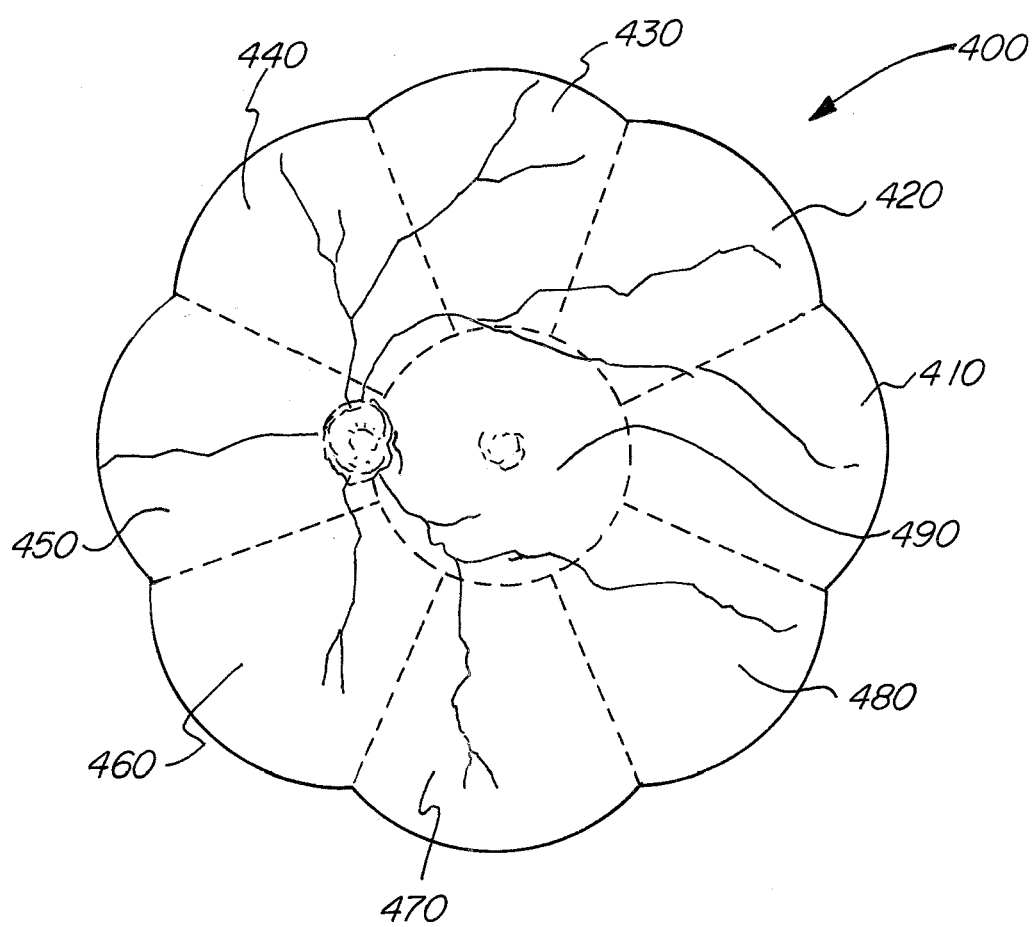

As shown in FIG. 6H, the composite image (400) displayed to the user may comprise multiple image segments "stitched" together, in this case nine image segments (410, 420, 430, 440, 450, 460, 470, 480, 490). In some embodiments, each of the nine image segments is captured by a separate camera. In other embodiments, the image segments are captured by a single camera or by any desired number of cameras. Once the captured image data is sent to the processor, the image segments are combined into one composite image to provide a larger picture of the eye anatomy and allow the physicians to view more surface area of the eye. The increased viewing area of the eye is essential for identifying and diagnosing various eye conditions.

One or more cameras (20) of the present invention may capture multiple images of the eye by "scanning" the eye. In other words, the camera (20) moves across the eye taking a series of consecutive images with an autofocus. These images are then displayed separately, or overlaid over one another to provide a 3D image, or are combined to provide a composite image, as described above. In one embodiment, the camera (20) moves in a direction substantially parallel to a horizontal axis of the eye and/or a vertical axis of the eye, as shown in FIG. 6A. In other embodiments, the camera moves in any desired direction with respect to the eye.

Two or more cameras may also be used to "scan" the eye. In some embodiments, two cameras are used wherein each camera is positioned at a different angle towards the eye. The cameras may start in a position wherein their view vectors overlap inside the eye, such as shown in FIG. 6E, and then move outwards such that the view vectors of each camera move away from each other, or diverging. This will provide an initial overlapping image and a series of subsequent images capturing the anatomy of the outer edges of the eye, which can then be combined or "stitched" together to provide a detailed composite image of the eye. In other embodiments, the two cameras start in a position where their view vectors are directed away from each other and then move towards each other until their view vectors overlap, or converge.

In another advantageous embodiment of the present invention, stereo camera is used to visualize the eye anatomy. The stereo camera includes two or more lenses, each with a separate image sensor. This allows the camera to simulate human binocular vision, making it possible to capture three-dimension images. The two or more image sensors are CMOS type sensors or any other suitable sensors, used together with one or more illumination sources. Each of the sensors captures an image from a different angle/position with respect to the eye. Then, the images are processed and displayed to the user as a single 3D image.

The device of the present invention utilizes a tracking system to track the motion of the eye and within the eye to adjust the cameras (20) to always obtain a clear and accurate image of the eye anatomy. Two different types of the tracking system are used. A first tracking system utilizes one or more cameras that track the motion of the eyeball itself. In order words, when the patient moves hers/his eyeball to look in a different direction, the cameras automatically adjust to that movement. This is accomplished by locating and recording certain landmarks or biomarkers within the eye, such as, for example 3 o'clock and 5 o'clock positions of the pupil, and then tracking the movement of those landmarks or biomarkers to determine a new position. Any suitable tracking mechanism may be use to accomplish this step. Then, the cameras and/or the entire housing moves to adjust the position with respect to the eye. It is understood that any other suitable tracking points or landmarks within the eye may also be used in this system.

A second tracking system tracks any motion within the eye. For example, the system tracks dilation/contraction of an iris and/or pupil of the eye, or movement of protein or crystalline material or other structures within the eye. This is accomplished by focusing one or more cameras on a particular structure or tissue in the eye and then automatically adjusting the position of the cameras as the structures/tissues move within the eye to maintain a laser focus on moving structures and/or tissues. Again, any suitable tracking mechanism is used for this step. In advantageous embodiments, both the first and second tracking systems are used in combination to track movement of the eye and structures within the eye to obtain a clear and accurate image of the eye anatomy.

Various suitable actuators may be used with the system (10). In the embodiment shown in FIG. 3, the system (10) includes a track (24) coupled to the eye wear housing (12) and extending longitudinally from one side of the housing to the other. The coupling members (16) with the cameras (20) positioned thereon are movably coupled to the track (24) by, for example, electrically driven motors, such that each of the coupling members (16) moves along the track in a longitudinal direction substantially parallel to the horizontal axis of the eye, as shown in this figure. In this embodiment, the cameras (20) are moved from a first position having a view vector along the first axis to a second position having a view vector along a second axis, wherein the second axis is substantially parallel to the first axis.

The actuator further includes a controller (52) that communicates with the coupling members (16) and/or track (24) to enable manipulation of the cameras (20) by a user/physician. The controller (52) may communicate via a cable connection (51) or wirelessly (53). In some advantageous embodiments, the controller (52) actuates each of the coupling members (16) individually or as a unit. In additional advantageous embodiments, each of the cameras (20) has a separate actuator and is actuated separately from the other cameras.

Figure 7A:
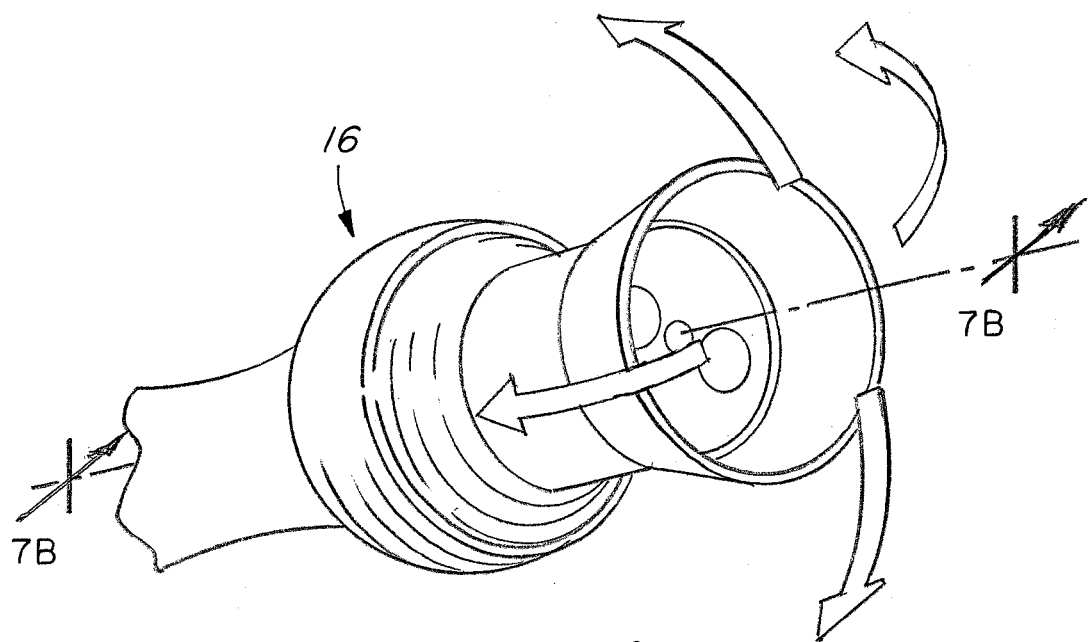
FIG. 7A is an enlarged perspective view of the camera of the system for visualization of eye anatomy of FIG. 1.
Figure 7B:
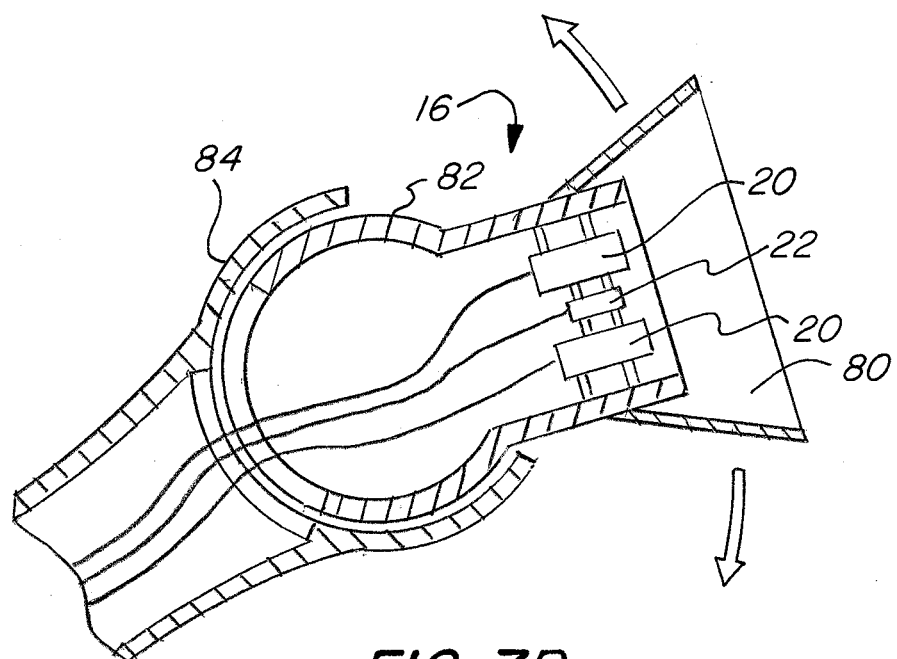
FIG. 7B is a cross-sectional view of the camera of FIG. 7A, taken along the line "7B-7B".

One exemplary embodiment of the coupling member (16) is shown in FIGS. 7A and 7B. The coupling member (16) includes a housing (82) that houses the cameras (20) and the illumination device (22). The housing (82) has a screen (80) at its proximal end made with any suitable material. The screen (80) may be completely transparent and function as a protective film between the cameras and the person's eye. In some advantageous embodiments discussed further below, the screen also functions to display an object to the user to facilitate enhanced imaging of the eye anatomy. In yet further embodiments, the screen (80) may be a lens to further improve the imaging of the eye.

A distal end of the housing (82) has a ball-like shape and mates with a socket-like portion (84) of the coupling member. This ball and socket configuration of the actuator enables rotary movement of the cameras in all directions, as shown in FIG. 7A. This, in turn, allows the cameras to capture a wide angle of view of the eye anatomy, and in particular, the eye retina. The actuation of the housing portions (82) and (84) is controlled via the controller coupled to the device, or may be actuated manually by adjusting the position of the cameras in front of the person's eyes. In this embodiment, when the housing portion (82) pivots in the housing portion (84), the cameras (20) are moved from a first position having a view vector along the first axis to a second position having a view vector along a second axis, wherein the second axis is angularly offset from the first axis. The housing portion (84) can be arranged in system for facilitating translational movement of the housing, such as the system employing a track (24) described above, such that the cameras (20), in addition to pivoted, can also be translated side to side or up and down.

As discussed above and also shown in FIG. 8, in some advantageous embodiments, the system also includes a screen (90) positioned between the cameras (92) and a person's eye (94). The screen (90) may be attached to the coupling members (16) or may be provided as a separate layer between the coupling members and the eye. The screen is made of any suitable substantially transparent material capable of displaying an image (96) to a user. The image (96) is displayed as a static image or a dynamic image. Any type of image may be displayed, such as, for example, a red dot or a moving car. The screen (90) is coupled to the processor and the controller via a wired or wireless connection.

When in use, the system (10) is positioned over the person's eye(s) and the cameras are placed adjacent to the eye(s). In some advantageous embodiments, a diameter of the iris is measured via any suitable measurement device. Data about the measured diameter is transmitted to a processor to determine a target opening. Based on this data, the processor then sends information to a controller for controlling actuation of the cameras to obtain wide angle view images of the eye anatomy.

Figure 8:
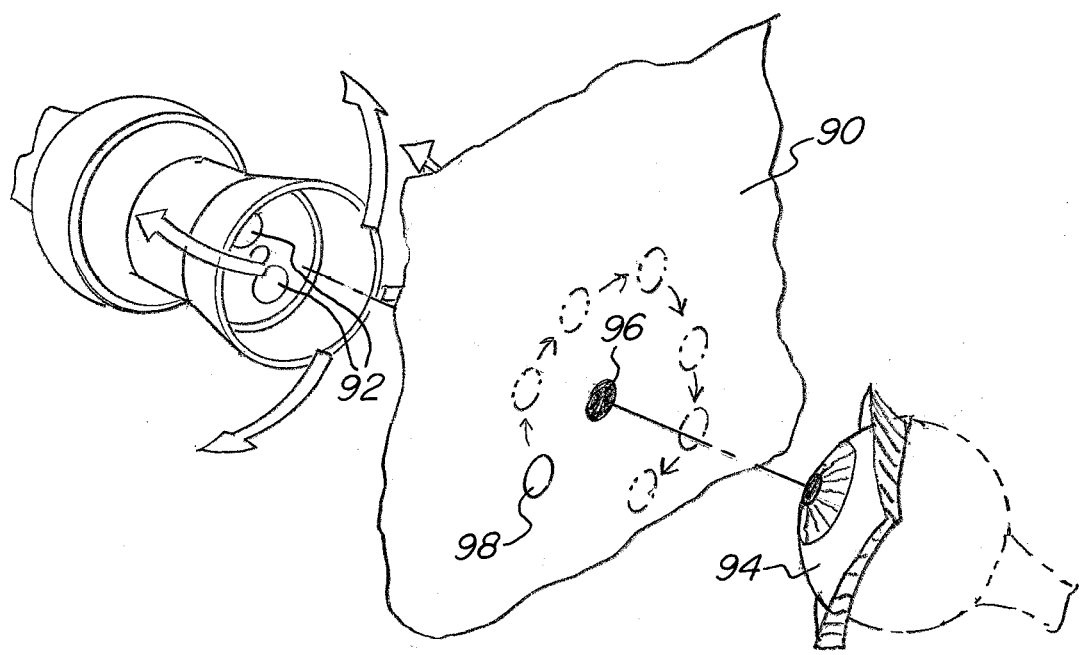
FIG. 8 is a partially schematic view of the system of FIG. 1 positioned in front of a person's eye.

As shown in FIG. 8, a static image (96) is then shown on the screen (90) and a person is instructed to focus their eye(s) of the static image. As the person's eye(s) remain focused, one or more cameras are actuated to view inside the eye(s) at different angles to obtain a wide angle of view. The cameras may move individually to obtain images at different angles, or may move as a unit.

In other embodiments, a dynamic image (98) is shown on the screen (90), and a person is instructed to follow the movement of the image on the screen. While the person's eye(s) are following the dynamic object (98), one or more cameras are also actuated to move around and obtain various angles of view of the eye anatomy. Again, the cameras may be actuated separately at different angles or may move together as a unit. In one advantageous embodiment, the system may utilize software that enables the cameras to follow the image from the screen that is reflected from the eye(s).

Once the imaging data is captured by one or more cameras, the data is transmitted to the processor for processing. Then, the processed image data is transmitted to the display for viewing by the physician. In some advantageous embodiments, the image data is stored on the storage device for later retrieval.

Figure 9:
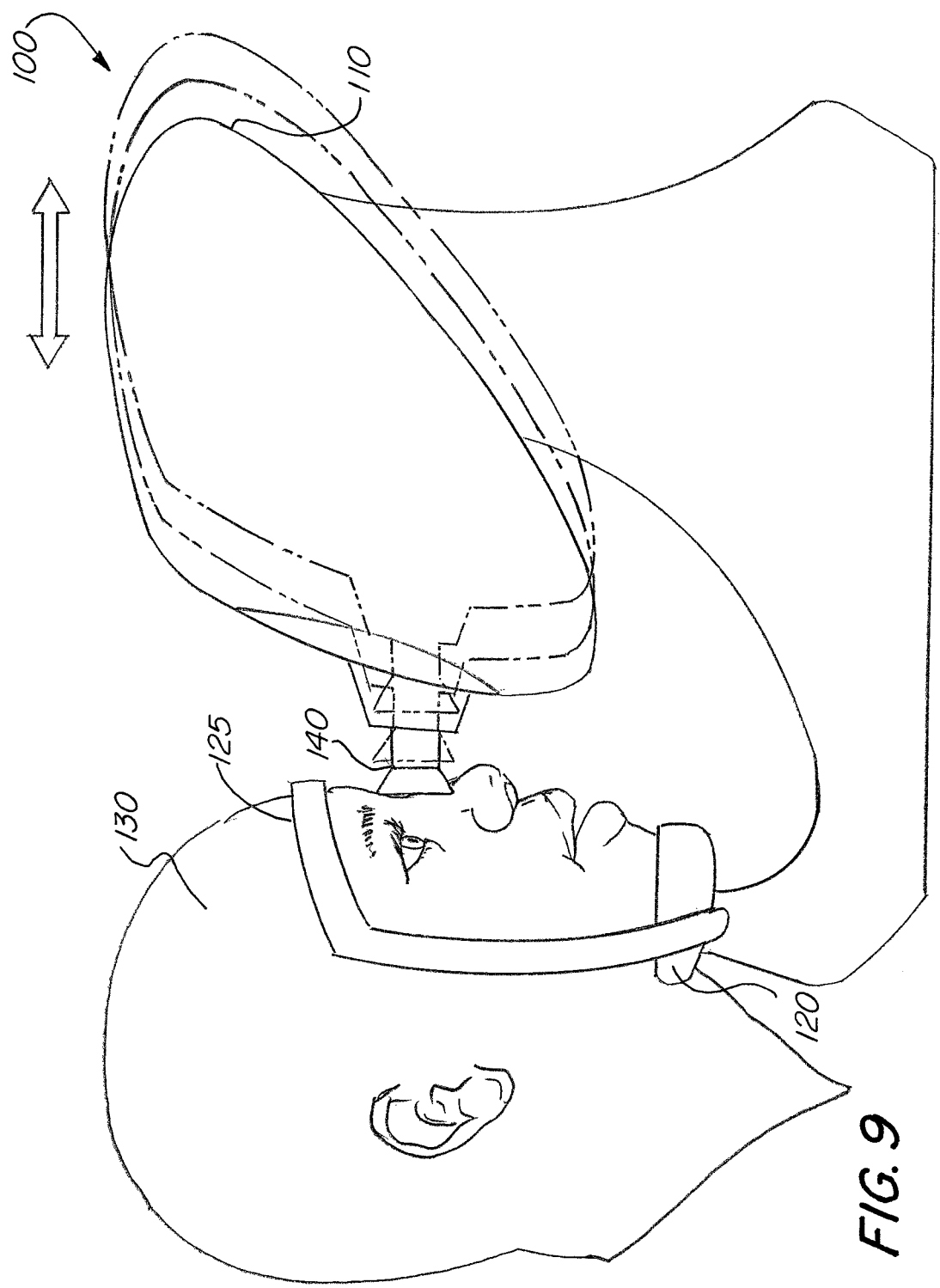
FIG. 9 is a side view of another housing embodiment of the system for visualization of eye anatomy in accordance with the present invention.
Figure 10:
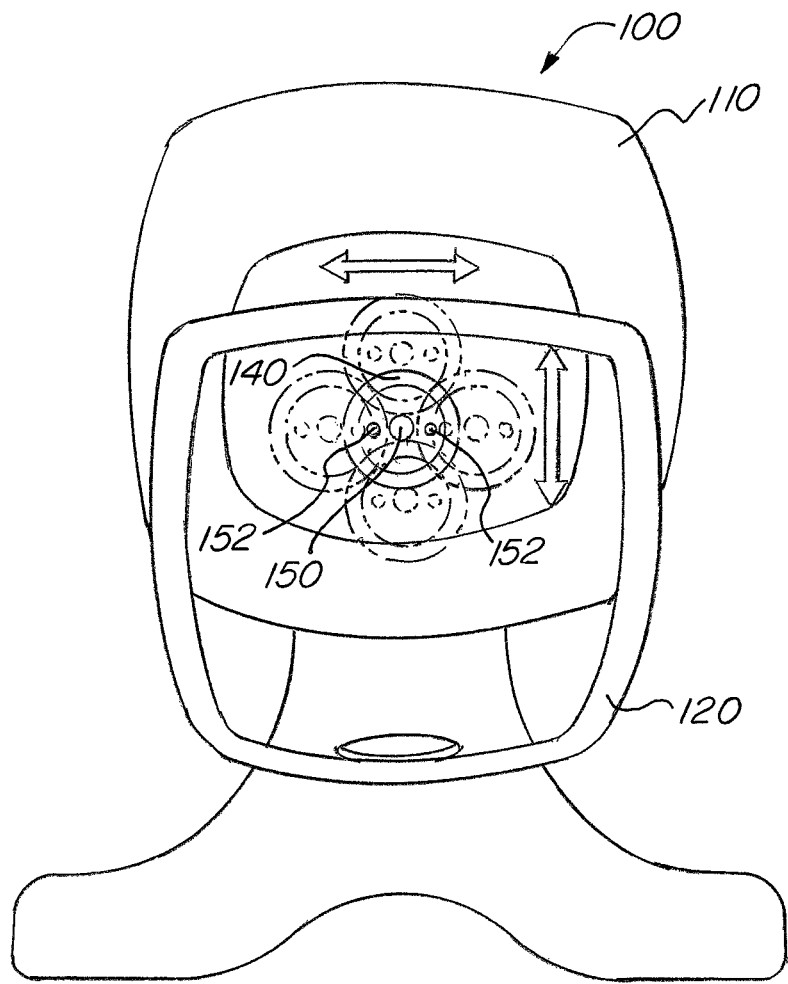
FIG. 10 is a front view of the system of FIG. 9.

FIGS. 9 and 10 illustrate another exemplary embodiment of the system of the present invention. In this embodiment, the system (100) is a standalone unit having a housing (110) that can be placed on any flat surface, such as a table, or can have a support unit for placement of the housing on the floor. The housing (110) includes a chin rest (120) and a forehead rest (125) or similar structures to position and align a person's head. The housing further includes a camera housing (140) movably coupled to the main housing (110). The camera housing (140) has one or more cameras (150) and one or more illumination devices (152) positioned therein, as shown in FIG. 10. It is understood that two camera housings may be provided, each with one or more cameras and illumination devices, to provide images of each eye.

As shown in FIG. 9, the top portion of the housing (110) with the camera housing (140) is movable in a direction toward and away from the person's head. The movement of the housing (110) is controlled by an internal controller positioned on the housing or an external controller positioned remotely and connected to the housing via a wired or wireless connection. When in use, once the person's head is positioned in the chin rest and the forehead rest, the cameras may be positioned at a desired distance from the person's eye(s) by actuating the housing in the direction shown in this figure.

Once the housing (110) is positioned at a desired distance from the eye(s), the camera housing (140) is actuated in directions substantially parallel to the vertical and horizontal axes of the eye to get a wide angle view of the eye anatomy. The actuation is controlled by the internal or external controller, as discussed above. While the camera housing (140) is being actuated, the chin rest (120) and the forehead rest (125) remain stationary to maintain the person's head (130) and eye(s) in the same position. If two camera housings are provided, each of the housings may move separately from the other, or the two housings may move together as a unit.

In some advantageous embodiments, as discussed in more detail above in connection with FIG. 8, a screen may be provided between the cameras (150) and the person's eye(s). A static and/or dynamic image is shown on the screen and the person is asked to focus on the image while the cameras (150) move around to capture images of the eye anatomy. Once the image data is captured by the cameras, it is sent to a processor via a wired or wireless connection. The processor processes the image data and displays it on a display to be viewed by a physician. The image data may also be stored on an internal or external storage device for later retrieval.

Figure 11:
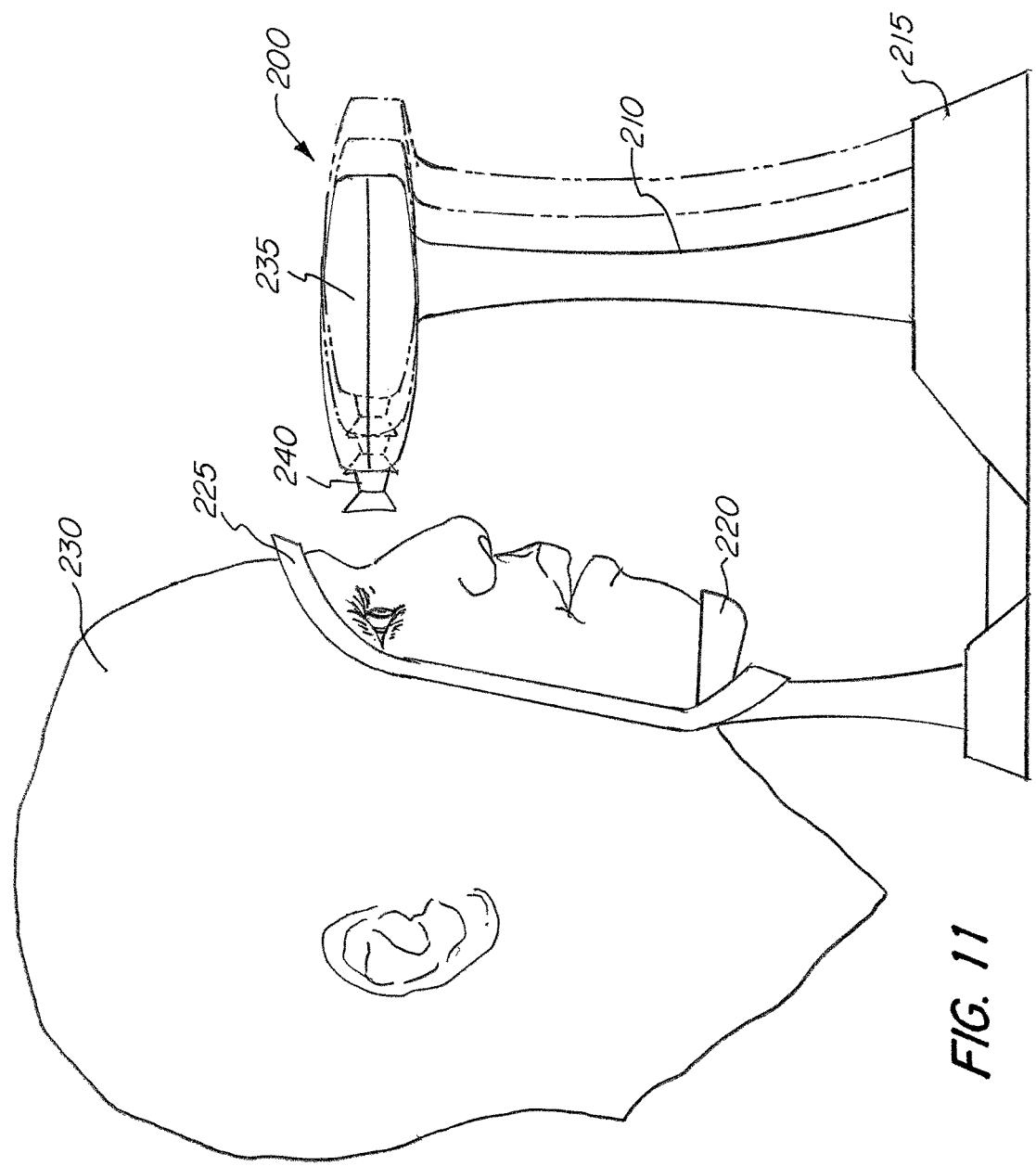
FIG. 11 is a side view of a further housing embodiment of the system for visualization of eye anatomy in accordance with the present invention.
Figure 12:
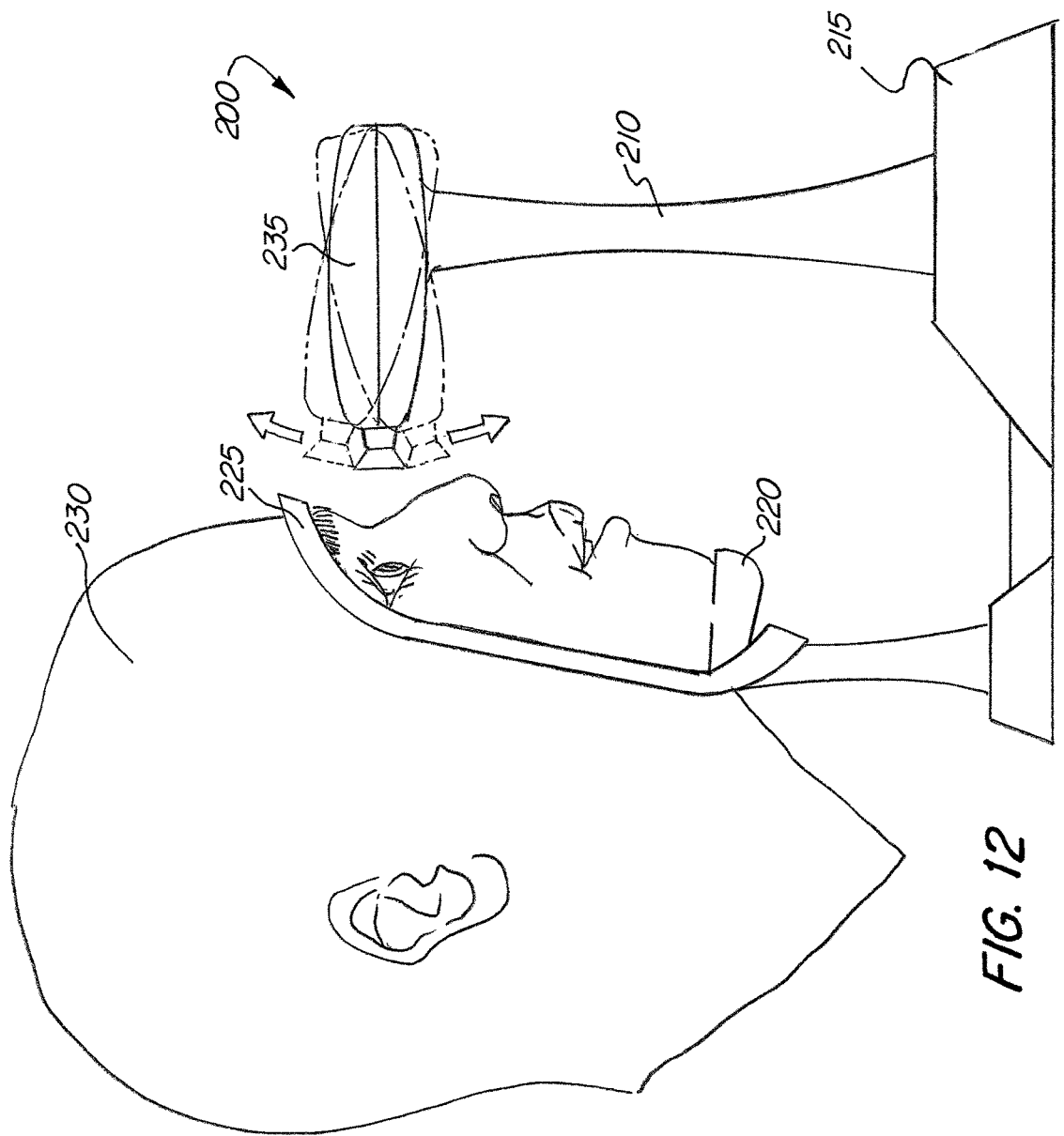
FIG. 12 is another side view of the system of FIG. 11.
Figure 13:
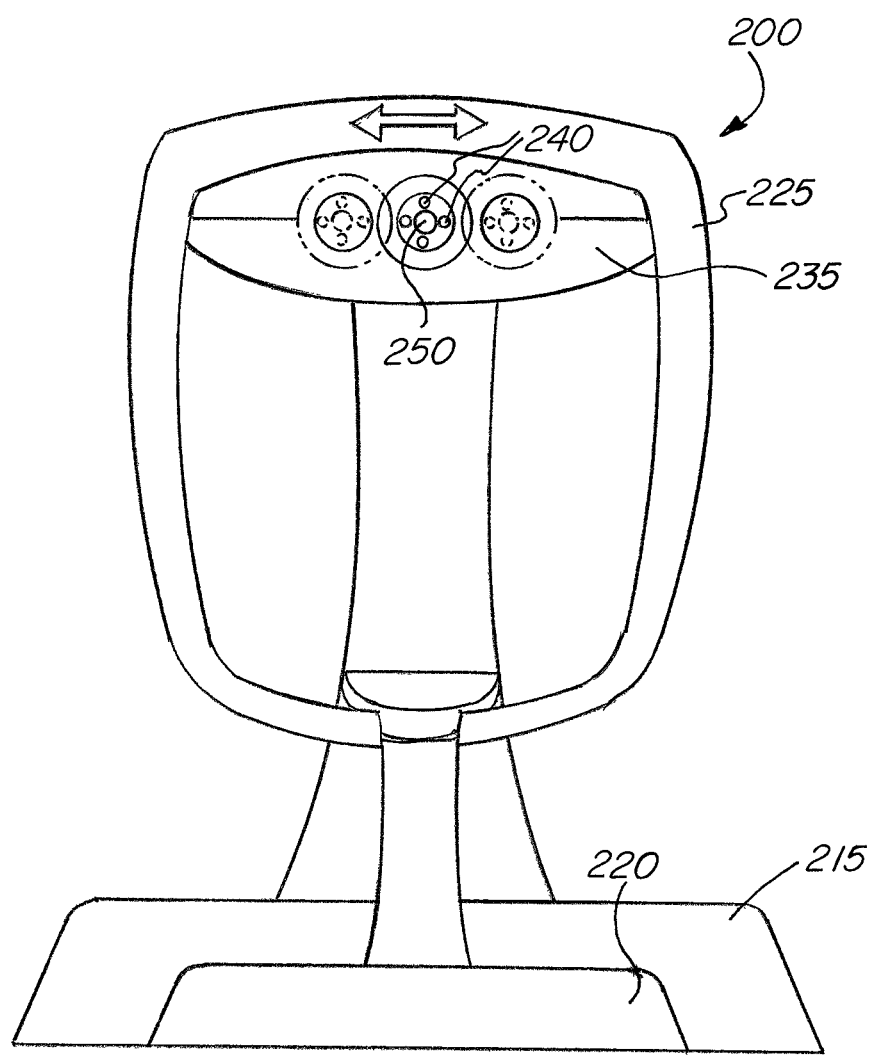
FIG. 13 is a front view of the system of FIG. 11.

Yet another exemplary embodiment of the system for visualization of eye anatomy of the present invention is shown in FIGS. 11-13. The system includes a housing (210) that has a movable base part (215), a movable camera housing part (235), a chin rest (220) and a forehead rest (225). Similarly to the device shown in FIGS. 9-10, the housing (210) is a standalone unit that can be placed on any flat surface or can have a support unit for placement of the housing on the floor.

The camera housing part (235) has one or more cameras (240) and one or more illumination devices (250) positioned therein, as shown in FIG. 13. It is understood that two camera housings may be provided in accordance with the present invention, and each housing may have one or more cameras and illumination devices positioned therein.

As shown in FIG. 11, the housing (210) is movable within the base (215) such that the camera housing portion (235) is positioned further or closer to a person's head (230) positioned in the chin rest (220) and the forehead rest (225). The movement of the housing is controlled by a controller positioned on the housing or positioned remotely and connected to the housing via a wired or wireless connection.

Once the camera housing (235) is positioned at a desired distance from the eye(s), the camera housing (230) may be actuated in a direction substantially parallel to the vertical axis of the eye, as shown in FIG. 12. Additionally, the camera housing (230) may be actuated in a direction substantially parallel to the horizontal axis of the eye(s), as shown in FIG. 13. This allows the cameras (250) to capture a wide angle view image of the eye anatomy. The actuation is controlled by the internal or external controller, as discussed above. If two camera housings are provided, each of the housings may move separately from the other, or the two housings may move together as a unit. The image data captured by the cameras is sent to a processor via a wired or wireless connection, and then the processed data is sent to a display to be viewed by a physician. The image data may also be stored on an internal or external storage device for later retrieval. The camera housing (235) may also include a screen positioned between the cameras (250) and the person's eye(s) to display a static and/or dynamic image to the person.

It should be noted that, while only certain movements of the cameras (20) are described when discussing the illustrations of particular embodiments, any combination of the camera movements described in FIGS. 6B-E, including all such movements, can be implemented in any individual embodiment by combining the various actuation mechanisms described herein. It should also be noted that, in any of the embodiments described herein, the camera(s) adjacent one eye may be moved together with or separately from the camera(s) adjacent the other eye. Likewise, in any of the embodiments described herein, the camera(s) adjacent a single eye may be moved together as a unit or separately.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of visualization of eye anatomy, comprising the steps of:
engaging a patient's head with a housing having a first camera and a second camera coupled thereto such that said first and second cameras are positioned adjacent to at least one eye of the patient, wherein said first camera has a view vector along a first axis when in a first position and said second camera has a view vector along a second axis when in a first position, wherein the view vector of the first camera extends along a viewing axis that defines a center of a field of view of the first camera and the view vector of the second camera extends along a viewing axis that defines a center of a field of view of the second camera; and
moving said first and second cameras to a second position;
wherein, when said first camera is in the second position, its view vector is along a third axis that is offset from the first axis, and wherein, when said second camera is in the second position, its view vector is along a fourth axis that is offset from the second axis.

2. The method of claim 1, wherein the third axis is angularly offset from the first axis.

3. The method of claim 1, wherein the third axis is substantially parallel to the first axis.

4. The method of claim 1, further comprising using a processor to process image data captured by at least one of the first and second cameras.

5. The method of claim 1, wherein the first and second cameras are positioned adjacent the same eye of the patient.

6. The method of claim 1, further comprising providing illumination with at least one illumination device positioned adjacent at least one of the first and second cameras.

7. The method of claim 6, wherein the at least one illumination device comprises a light source having at least one of a visible, ultraviolet, infrared and near infrared spectrum.

8. The method of claim 1, wherein the housing is a standalone unit further comprising a positioning member for positioning the eye relative to at least one of the first and second cameras.

9. The method of claim 1, further comprising using a storage device to store image data captured by at least one of the first and second cameras.

10. The method of claim 1, further comprising using a 2-D or 3-D display coupled to at least one of the first and second cameras to display image data captured by the camera.

11. The method of claim 1, wherein at least one of the first and second cameras comprises at least one lens and at least one imaging sensor.

12. The method of claim 11, wherein the imaging sensor comprises a CMOS sensor.

13. The method of claim 1, wherein at least one of the first and second cameras is moved to the second position via a track coupled to the housing and a moving member coupled to the camera, wherein the moving member moves along the track.

14. The method of claim 1, wherein at least one of the first and second cameras is moved to the second position via a ball and socket actuator that enables rotary movement of the camera.

15. The method of claim 1, wherein the first and second cameras are positioned adjacent a first eye of the patient, further comprising at least one additional camera coupled to the housing such that the at least one additional camera is positioned adjacent a second eye of the patient.

16. The method of claim 15, wherein the first and second cameras positioned adjacent the first eye move separately from said at least one additional camera positioned adjacent the second eye.

17. The method of claim 15, wherein the first and second cameras position adjacent the first eye and said at least one additional camera positioned adjacent the second eye move together as a unit.

18. The method of claim 1, wherein the first camera is positioned adjacent a first eye of the patient, and the second camera is positioned adjacent a second eye of the patient.

19. The method of claim 1, further comprising tracking the movement of the eye with a tracking system.

20. The method of claim 1, further comprising tracking movement of at least one structure and/or material within the eye with a tracking system.

* * * * *